United States Patent [19]
Khalkhali

[11] Patent Number: 5,895,640
[45] Date of Patent: Apr. 20, 1999

[54] NUCLEAR MEDICINE TECHNIQUES FOR DETECTING CARCINOMA IN THE DENSE BREAST

[75] Inventor: Iraj Khalkhali, Rancho Palos Verdes, Calif.

[73] Assignee: Harbor-UCLA Research and Education Institute, Torrance, Calif.

[21] Appl. No.: 08/740,639

[22] Filed: Oct. 31, 1996

Related U.S. Application Data

[63] Continuation-in-part of application No. 08/253,419, Jun. 3, 1994, Pat. No. 5,595,177
[60] Provisional application No. 60/006,485, Nov. 9, 1995.

[51] Int. Cl.⁶ .............................. A61K 51/04; A61B 5/05
[52] U.S. Cl. .................. 424/1.65; 600/429; 600/431; 600/436
[58] Field of Search ............................. 424/1.61, 1.65, 424/1.69, 1.73, 1.77, 1.81, 1.85, 1.89, 1.37; 600/431, 429, 436; 534/10, 14

[56] References Cited

U.S. PATENT DOCUMENTS

| | | | |
|---|---|---|---|
| 4,875,478 | 10/1989 | Chen | 128/303 |
| 5,056,523 | 10/1991 | Hotchkiss, Jr. et al. | 128/653 |
| 5,078,142 | 1/1992 | Siczek et al. | 128/653.1 |
| 5,209,232 | 5/1993 | Levene | 128/653 |
| 5,289,520 | 2/1994 | Pellegrino et al. | 378/37 |
| 5,595,177 | 1/1997 | Mena et al. | 128/653.1 |

*Primary Examiner*—Jose' G. Dees
*Assistant Examiner*—Michael G. Hartley
*Attorney, Agent, or Firm*—Fulwider Patton Lee & Utecht, LLP

[57] ABSTRACT

A nuclear medicine technique for detecting and localizing carcinomas in the breasts of patients with dense breast. In the method, a patient with dense breast is administering a dose of Technetium-99m Sestamibi, or another nuclear medicine substance which selectively accumulates in breast carcinomas. The breast is then imaged with a nuclear medicine detector to image the carcinomas with the accumulated nuclear medicine agent and localize the carcinomas in real time and in three dimensions. The imaging can be done in a first plane with the detector perpendicular to a lateral side of the breast and also in a second plane parallel to the patient's chest wall.

13 Claims, No Drawings

NUCLEAR MEDICINE TECHNIQUES FOR DETECTING CARCINOMA IN THE DENSE BREAST

RELATED APPLICATIONS

This application claims benefit of U.S. Provisional application Ser. No. 60/006,485, filed Nov. 9, 1995 and this application is a continuation-in-part of Ser. No. 08/253,419, filed Jun. 3, 1994, now U.S. Pat. No. 5,595,177, issued Jan. 21, 1997.

BACKGROUND OF THE INVENTION

1. Field of the Art

This invention relates to the field of breast lesion localization and biopsy, and more particularly to a method for localizing a breast lesion by nuclear medicine detection in three dimensions and in real-time.

2. Description of the Prior Art

The occurrence of breast cancer is a leading cause of death for women. Women are advised to conduct breast self examination for palpable lumps or bumps on a monthly basis, and after the age of 40, to undergo mammography at least on a bi-annual basis in order to detect nonpalpable lesions. Presently, special roentgenography, or x-ray techniques for photographically studying the mammary gland, or breast, are utilized to locate lesion with greater success than with self-examination, particularly with small lesion located deep in the breast. However, one major problem with traditional x-ray mammography is that there is little selectivity in what is imaged. In addition to malignant carcinoma tumors, generally harmless calcifications, proliferative changes., fibroadenomas, and fibrocystic changes show up. Indeed, while x-ray mammography has a high sensitivity of 85–90%, it currently predicts malignancy in only about 20–30% of mammography suspicious lesions. Since the radiologist has great difficulty in distinguishing malignancy from harmless lesions, biopsy and tissue cultures must be carried out to determine if the lesion is malignant. In fact, in around 80% of the cases where biopsies are performed, the lesions prove not to be malignant.

In order to effectively conduct the x-ray mammography, the patient's breast being imaged must be compressed with great and uncomfortable force to squeeze the breast to a thickness of about three to four and a half centimeters so that the x-rays can adequately penetrate the breast and develop the film lying behind the breast. This process must be conducted in two separate planes. First, the breast is compressed in a horizontal plane, so a cranial and caudal projection can be taken. The next projection taken is a mediolateral oblique view, wherein the breast is compressed in a vertical plane. These two initial views taken together make up the screening mammography.

The radiologist will then read the x-ray negatives to determine if there are any lesions or other signs of lesions in the breast. If the radiologist sees any suspicious lesions, then "special views" are taken. Actually, the same views as in a screening are carried out, except that the compressed breast is slightly displaced from the film plate to effect magnification of any lesions in the breast. If the radiologist finds a suspicious lesion, a biopsy needle will be inserted into the lesion site of the anesthetized breast.

After the needle is placed in the breast, another x-ray image will be taken, to determine how close the tip of the needle is to the lesion. Several adjustments of the needle and several x-ray photographs may be required to position the needle at the lesion site. Once the biopsy needle is positioned near the lesion site, a hooked guide wire will be pushed through the biopsy needle and hooked onto the lesion. The guide wire provides the surgeon with a traceable path to the lesion. The surgeon will then remove either a sample of the lesion (i.e. by aspiration biopsy), or the entire lesion in surgical biopsy procedure, and the tissue removed will be examined by the oncologist. This process is time consuming, painful, physically scaring, and expensive. The patient will then wait a few agonizing days to learn of the test results. Again, since by x-ray mammography the radiologist cannot readily distinguish between malignant and non-malignant lesions, when suspicious lesions are located, biopsy is required. Since statistically 80% of all lesions are non-malignant, present x-ray mammography technique results in many unnecessary biopsies.

Several approaches have been explored to better locate the position of the lesion in a patient's breast by x-ray mammography. U.S. Pat. No. 5,209,232 to Levene uses computerized device to accurately detect the position of lesions in the breast, and to position the biopsy needle. U.S. Pat. No. 5,289,520 to Pellegrino et al. and U.S. Pat. No. 5,078,142 to Siczek et al. provide automated breast lesion locator imaging and biopsy systems.

U.S. Pat. No. 5,056,523 to Hotchikiss, Jr. et al. discloses a device and method for precisely positioning the tip of a probe into a breast lesion. Radiopaque markers are used to identify the position of the lesion relative to a fenestrate compression grid. To determine the depth of the lesion in the breast, a certain amount of trial and error is required. A similar system is provided by the method and apparatus of U.S. Pat. No. 4,875,478 to Chen. The Chen apparatus used a radiolucent compression support plate with calibration marks, with a movable biopsy needle support guide, so that the biopsy needle can be positioned with its tip in the lesion. Notwithstanding the improvements provided by these x-ray mammography devices, major problems remain in that many unnecessary biopsies will still be to be performed.

Another new, experimental method utilizes contrast material-enhanced magnetic resonance (MR) mammography, and is disclosed in "MR Mammographic Localization, Work in Progress", by K. Hussman et al. Radiology, Vol. 189, No. 3, pp. 915–917. By this method, after MR resonance enhancing agents are injected into the patient's bloodstream, her breast being examined is placed in an open box with two fenestrated perpendicular side walls. The position of the lesion in the X, Y and Z coordinates is noted, and the precise position of the biopsy needle will then be sought to be located. Since the magnetic resonance apparatus is quite narrow to enter, the needle must be inserted after the patient's breast is imaged. To avoid the breast shifting in the box, the breast is best temporarily adhered to the box with medical grade adhesive. The technique of the Hussman et al. device, is highly uncomfortable, cumbersome, and expensive, and makes this approach disfavored.

Recently, the use of Technetium-99m Sestamibi (sold under the name Cardiolite®, by the DuPont Merck Pharmaceutical Co., North Billerica, Mass.) has been explored to accurately detect the presence of carcinoma of the breast. See "Review of Imaging Techniques for the Diagnosis of Breast Cancer, a New Role of Prone Scintimammography using Technetium-99m Sestamibi", by I. Khalkhali, I. Mena, and L. Diggles, European Journal of Nuclear Medicine, Vol. 21, No. 4, April 1994, pp. 357–362, and "Prone Scintimammography in Patients with Suspicion of Carcinoma of the Breast", by I. Khalkhali, I. Mena, E. Jouanne, L. Diggles, R.

Venegas, J. Block, K. Alle, and S. Klein, Journal of American College of Surgeons, May 1994, Vol. 178, pp.491-97.

Scintimammography is the method to detect the presence of malignant tumors by radioactive substances which selectively accumulate in the malignant tumors, or carcinomas.

By utilizing the method of scintimammography with Technetium-99m Sestamibi, the inventor and others have reported a negative predictive value for the presence of carcinoma of 97.5%, a sensitivity of 96%, and a specificity of 85%. See U.S. patent application Ser. No. 08/253,419, filed June 3, 1994 now U.S. Pat. No. 5,595,177. By the method of scintimammography using Technetium-99m Sestamibi, malignant lesions as small as 2-3 mm or smaller can be diagnosed. In this methodology, a scintillation camera is used to detect the radiation given off from the Technetium-99m Sestamibi. In addition to scintillation cameras, newer semiconductor radioactive detectors, such as offered by the Vigirad company can be used, which does not specifically rely on scintillation, but nonetheless detects the radiation given off. Hereinafter, the term "scintimammography" shall refer not only to the method which uses a scintillation camera but also includes the method using newer semiconductor detectors.

The methodology of scintimammography has not yet heretofore been proven effective for localizing lesions in women with so called "dense breast". The term "dense breast" refers to the condition of the breast wherein the parenchyma is very fibrous and dense, which condition makes traditional mammography difficult since the dense breast is not easily compressed during mammography, and lesions in the dense breasts are often not palpable. Furthermore, under x-ray, tumors are hard to distinguish from dense breast tissue. There accordingly remains a need for a method for reliably localizing lesions in the dense breast.

In Radiology 1995; 196:421-426, the inventor and others report on the usefulness of the method of scintimammography in the complementary role of prone breast imaging for the diagnosis of breast carcinomas, and suggest that the method of scintimammography would be useful for imaging for cancerous tumors in women with dense breast.

In the Journal of Nuclear Medicine, 36(5), Abstract 52P, of Tuesday, Jun. 13, 1995, Proceedings of the 42nd Annual Meeting, the inventor herein and others report that in a side-by-side study of 48 patients who exhibited grade +3 or +4 dense breast received both mammographs and scintimammography, the results for scintimammography for the detection of breast carcinoma in patients with dense breast has far superior sensitivity and specificity than the method of mammography. Conducting mammographs of the dense breast is difficult. Since some 25 percent to 35 percent of mammographs demonstrate dense fibroglandular breast tissue, there remains a need for a method for accurately detecting for the presence of carcinomas in the dense breast.

DETAILED DESCRIPTION OF THE PREFERRED EMBODIMENT

The methodology of this invention can be employed by employing the device disclosed in U.S. patent application Ser. No. 08/253,419, filed Jun. 3, 1995, now U.S. Pat. No. 5,595,177, of which the Applicant herein is one inventor. The disclosure of U.S. patent application Ser. No. 08/253, 419, now U.S. Pat. No. 5,595,177 is incorporated herein by reference.

The methodology of the invention utilizes nuclear medicine techniques to detect for the presence of cancerous lesions in a woman's breast. The compound Technetium-99m Sestamibi (sold under the name Cardiolite®, by the DuPont Merck Pharmaceutical Co., North Billerica, Mass.) is a nuclear medicine agent which selectively accumulates in breast carcinomas, and which can be detected by nuclear medicine techniques, including scintimammography, as disclosed in U.S. patent application Ser. No. 08/253,419 now U.S. Pat. No. 5,595,177.

For women having +3 and +4 dense breast, as determined by the American College of Radiology Database System (BIRD™) 1993, Reston, Va., mammography is not very effective in detecting the presence of carcinomas because the tumors in the dense breast are not easily palpable, and the dense breast tissue looks very much like the carcinoma under mammograph. Under the American College of Radiology Database System, a +1 breast is classified as a "fatty breast", a +2 breast has 25% glandular tissue on mammograph, a +3 breast has 50% glandular tissue on mammograph, and a +4 breast has greater than 50% glandular tissue on mammograph. As the percentage of glandular tissue increases, the breast become more dense, and more difficult to compress and examine by palpitation and by mammograph.

A scintillation camera, or newer, semiconductor detectors can be used to detect and measure the radioactive particles emitted from the radioactive material which accumulates in breast carcinomas, and can thus be used to detect and localize the position of carcinomas in the breast of a woman.

Scintimammography was performed by using a rectangular head camera (Sophy-Camera DSZ; Sopha Medical Systems, Columbia, Md.) with a high-resolution collimator. Again, however, newer, digital cameras can also be utilized to detect the radioactive activity, and thus detect and localize carcinoma. Planar images were taken of patients in the prone position with the breast being examined pendulously protruding through an opening in a plastic table. The prone position allows a single breast to be imaged with the exclusion of any activity in the contralateral breast, and aids in maximum separation of breast tissue from the myocardium and liver.

Each patient received an intravenous injection with 20 mCi (740 MBq) dose of Tc-99m Sestamibi in the arm contralateral to the breast being examined. Lateral imaging with each breast in the prone position was performed for 10 minutes at 5 minutes and 1 hour after injection. In practice, the inventor has found that there are few advantages in taking images at 1 hour following injection compared to images taken at 5 minutes following injection.

In order to detect for cancers in a woman's axilla (armpit area), anterior upright chest scintimammography was performed for 10 minutes with the detector tilted 30° outwardly from the centerline between the breasts with her arms raised for depiction of the axilla. The patient will "hug" her breast being examined against the camera. This angle will reveal the presence of any activity in the lymph nodes in the axilla which would indicate the cancer metastasized there.

In addition to this, posterior oblique imaging at 30° was performed if a lesion was seen near the chest wall. The whole-body radiation dose was approximately 0.3 rad (3mGy), and the breast received minimal radiation, according to the Cardiolite package insert, DuPont Merck Pharmaceutical, 1994).

All images were routinely evaluated on dedicated nuclear medicine computer monitors as well as on hard copy. A negative classification indicated minimal, symmetrical, bilateral, and uniform breast uptake equal to soft-tissue uptake of the Cardiolite compound. A probable negative uptake indicated mild to moderate bilateral or unilateral diffuse uptake, probably abnormal was indicated by a probable increased zone of uptake, and abnormal was indicated by a definite focal zone of increased uptake.

A group of 48 patients aged 38±7.1 (mean ± S.D.) women who exhibited +3 or +4 dense breast according to the American College of Radiology were examined both by mammography and scintimammography. The results indicate the superiority of the nuclear medicine technique from a standpoint of sensitivity and specificity in detecting breast cancer. The results were as follows:

| PATHOLOGY | | | | |
|---|---|---|---|---|
| Pathology Scintimammography (SAM) | | | Pathology Mammography (MAMM) | |
| | CANCER | BENIGN | CANCER | BENIGN |
| SAM + | 15 | 3 | MAMM + 13 | 17 |
| SAM − | 1 | 29 | MAMM − 3 | 15 |
| Sensitivity = 15/16 = 93.7% | | | Sensitivity = 13/16 = 81.2% | |
| Specificity = 29/32 = 90.6% | | | Specificity = 15/32 = 46.8% | |

The method of the invention of using nuclear medicine for diagnosis of breast cancer in difficult cases, such as where the patient has dense breast, lumpy breast, internal scarring in the breast, and a breast with many nodules is superior in its selectivity and specificity to traditional X-ray mammography. Overall in all age categories, approximately 25% of women have dense breast. In the age category of 40 to 49 years old about 35% of women have dense breast. Regardless of age category, another 5 to 10% of woman have other conditions which are not conducive to X-ray mammography, such as many benign nodules in the breast, lumpy breasts, and scarring. There is accordingly a large population of woman for whom the methodology of the invention is particularly well-suited, although the method is also superior to X-ray mammography for woman without these conditions. After a carcinoma is located, it can be localized, if palpable, by the surgeon and biopsied. If the carcinoma is not palpable and cannot be easily localized by the mammography, the carcinoma can be localized by the technique and device described in U.S. patent application Ser. No. 08/253,419, filed Jun. 3, 1995 now U.S. Pat. No. 5,595,177.

I claim:

1. A nuclear medicine technique for detecting and localizing carcinomas in the breasts of patients with dense breast, comprising:

(a) administering to a patient with dense breast a nuclear medicine agent which selectively accumulates in breast carcinomas; and (b) imaging a patient's breast with a detector to detect and localize the carcinomas with accumulated nuclear medicine agent in real time and in three dimensions.

2. The nuclear medicine technique for detecting and localizing carcinomas in the breasts of patients with dense breast of claim 1, wherein the nuclear medicine agent comprises the compound Technetium-99m Sestamibi.

3. The nuclear medicine technique for detecting and localizing carcinomas in the breasts of patients with dense breast of claim 1, wherein the detector comprises one of a scintillation camera and a semiconductor detector, said detector being used to detect and measure the radioactive particles emitted from the nuclear medicine agent.

4. The nuclear medicine technique for detecting and localizing carcinomas in the breasts of patients with dense breast of claim 1, wherein the imaging takes place with the patient lying in a prone position with the patient's breast protruding downwardly.

5. The nuclear medicine technique for detecting and localizing carcinomas in the breasts of patients with dense breast of claim 1, wherein the technique is used for posterior oblique imaging.

6. The nuclear medicine technique for detecting and localizing carcinomas in the breasts of patients with dense breast of claim 2, wherein a dose of about 20 mCi of Technetium-99m Sestamibi is intravenously injected in the arm contralateral to the breast.

7. The nuclear medicine technique for detecting and localizing carcinomas in the breasts of patients with dense breast of claim 4, wherein the patient's breast is imaged in a first plane with the detector perpendicular to a lateral side of the breast and also in a second plane parallel to the patient's chest wall, to thereby detect and localize the carcinomas in three dimensions and in real time.

8. A nuclear medicine technique for detecting and localizing carcinomas in the breasts of patients with dense breast, comprising:

(a) administering to a patient with dense breast a dose of Technetium-99m Sestamibi, which selectively accumulates in breast carcinomas; and (b) imaging the breast with a nuclear medicine detector to localize the carcinomas with accumulated nuclear medicine agent in real time and in three dimensions.

9. The nuclear medicine technique for detecting and localizing carcinomas in the breasts of patients with dense breast of claim 8, wherein the detector comprises one of a scintillation camera and a semiconductor detector, said detector being used to detect and measure the radioactive particles emitted from the nuclear medicine agent.

10. The nuclear medicine technique for detecting and localizing carcinomas in the breasts of patients with dense breast of claim 8, wherein the imaging takes place with the patient lying in a prone position.

11. The nuclear medicine technique for detecting and localizing carcinomas in the breasts of patients with dense breast of claim 10, wherein the patient's breast is imaged in a first plane with the detector perpendicular to a lateral side of the breast and also in a second plane parallel to the patient's chest wall, to thereby detect and localize the carcinomas in three dimensions and in real time.

12. The nuclear medicine technique for detecting and localizing carcinomas in the breasts of patients with dense breast of claim 8, wherein the technique is used for posterior oblique imaging.

13. The nuclear medicine technique for detecting and localizing carcinomas in the breasts of patients with dense breast of claim 8, wherein a dose of about 20 mCi of Technetium-99m Sestamibi is intravenously injected in the arm contralateral to the breast being examined.

* * * * *

UNITED STATES PATENT AND TRADEMARK OFFICE
CERTIFICATE OF CORRECTION

Page 1 of 3

PATENT NO.  : 5,895,640
DATED       : Apr. 20, 1999
INVENTOR(S) : Iraj Khalkhali It is certified that error appears in the above-identified patent and that said Letters Patent is hereby corrected as shown below:

Front page, after listing of "U.S. PATENT DOCUMENTS", add the following publications:

--N. Nagarai, A. Waxman, J. Silverman, M. Jochelson, S. Kahn, L. Mamsio, J. Yadager and E. Phillips, "COMPARISON OF TC-99M SESTAMIBI (MIBI) AND MRI IN PATIENTS WITH DENSE BREAST", Cedar Sinai Medical Center, Los Angeles, CA: Proceedings of the 41st Annual Meeting, Vol. 35, Number 5, May 1994

Cumali Aktolum, M.D., Hikmet Bayhan, M.D. and Metin Kir, M.D., "Clinical Experience with Tc-99m MIBI Imaging in Patients with Malignant Tumors, Preliminary Results and Comparison with TI-201", Clinical Nuclear Medicine, March 1992, Vol. 17, pages 171-176

R.J. Campeau, M.D., K.A. Kronemer, M.D. and C.M. Sutherland, M.D., "Concordant Uptake of Tc-99m Sestamibi and TI-2012 in Unsuspected Breast Tumor", Department of Radiology and Surgery, Tulane University Medical Center, pages 936-937 (1992)

Z. Burak, M. Argon, A. Memis, S. Erdem, Z. Balkan, Y. Duman, E. E. Ozkilic, "Evaluation of Palpable Breast Masses with $^{99}Tc^m$ MIBI: A comparative study with mammography and ultrasonography", Nuclear Medicine Communications, 15, pages 604-612, (1994)

UNITED STATES PATENT AND TRADEMARK OFFICE
CERTIFICATE OF CORRECTION

PATENT NO. : 5,895,640
DATED : Apr. 20, 1999
INVENTOR(S) : Iraj Khalkhali

It is certified that error appears in the above-identified patent and that said Letters Patent is hereby corrected as shown below:

C.H. Kao, S.J. Wang, T.J. Liu, "The use of technetium-99m methoxyisobutylisonitrile breast scintigraphy to evaluate palpable breast masses", European Journal of Nuclear Medicine, Vol. 21, May 1994, pp. 432-436

Chia-Kung Kao, M.D., Shyh-Jen Wang, M.D. and Shin-Hwa Yeh, M.D., "Tc-99m MIBI Uptake in Breast Carcinoma and Axillary Lymph Node Metastases", Clinical Nuclear Medicine, pp. 898-900, Vol. 19 No. 10, Oct. 1994

Victor W. Lee, Eric J. Sax, David B. McAneny, Sidney Pollack, Rita A. Blanchard, Robert M. Beazley, Maureen T. Kavanagh and Robert J. Ward, "A Complementary Role for Thallium-201 Scintigraphy with Mammography in the Diagnosis of Breast Cancer", The Journal of Nuclear Medicine, Vol. 34, No. 12 (1993), pp. 2095-2100

Khalkhali, et al., Abstract # 208, Proceedings of the $42^{nd}$ Annual Meeting, Journal of Nuclear Medicine, page 52p, 36(5), June 13, 1995

K. Hussman, et al., "MR Mammographic Localization Work in Progress", Radiology, pages 915-917, Vol. 189, No. 3, (1993)

DuPont Merck Phamaceutical Co., "Cardiolite Kit for the Preparation of Technetium Tc-99m Sestamibi", (1994)

Iraj Khalkhali et al., "Review of Imaging Techniques for the Diagnosis of Breast Cancer, a New Role of Prone Scintimammography Using Technetium-99m Sestamibi", European Journal of Nuclear Medicine, pages 357-362, Vol. 21, No. 4, (1994)

UNITED STATES PATENT AND TRADEMARK OFFICE
CERTIFICATE OF CORRECTION

PATENT NO. : 5,895,640
DATED : Apr. 20, 1999
INVENTOR(S) : Iraj Khalkhali

It is certified that error appears in the above-identified patent and that said Letters Patent is hereby corrected as shown below:

Iraj Khalkhali et al., "Prone Scintimammography in Patients With Suspicion of Carcinoma of the Breast", <u>Journal of the American College of Surgeons</u>, pages 491-497, Vol. 178. (1994)

Iraj Khalkhali, et al., "Scintimammography: The Comlementary Role of Tc-99m Sestamibi Prone Breast Imaging for the Diagnosis of Breast Carcinoma", <u>Radiology</u>, pages 421-426, Vol. 196, No.2 (1995)--.

Signed and Sealed this

Twenty-sixth Day of October, 1999

*Attest:*

Q. TODD DICKINSON

*Attesting Officer*    *Acting Commissioner of Patents and Trademarks*

UNITED STATES PATENT AND TRADEMARK OFFICE
CERTIFICATE OF CORRECTION

PATENT NO. : 5,895,640
APPLICATION NO. : 08/740639
DATED : April 20, 1999
INVENTOR(S) : Khalkhali et al.

It is certified that error appears in the above-identified patent and that said Letters Patent is hereby corrected as shown below:

On the title page item (75), add --Ismael Mena--.

Signed and Sealed this

Thirtieth Day of December, 2008

JON W. DUDAS
*Director of the United States Patent and Trademark Office*